US010962752B2

(12) United States Patent
Judkewitz et al.

(10) Patent No.: US 10,962,752 B2
(45) Date of Patent: Mar. 30, 2021

(54) METHOD AND ARRANGEMENT FOR IDENTIFYING OPTICAL ABERRATIONS

(71) Applicant: CHARITÉ—UNIVERSITÄTSMEDIZIN BERLIN, Berlin (DE)

(72) Inventors: Benjamin Judkewitz, Berlin (DE); Ioannis Papadopoulos, Berlin (DE)

(73) Assignee: CHARITÉ—UNIVERSITÄTSMEDIZIN BERLIN, Berlin (DE)

( * ) Notice: Subject to any disclaimer, the term of this patent is extended or adjusted under 35 U.S.C. 154(b) by 67 days.

(21) Appl. No.: 16/093,542

(22) PCT Filed: Apr. 12, 2017

(86) PCT No.: PCT/EP2017/058806
§ 371 (c)(1),
(2) Date: Oct. 12, 2018

(87) PCT Pub. No.: WO2017/178538
PCT Pub. Date: Oct. 19, 2017

(65) Prior Publication Data

US 2019/0204574 A1 Jul. 4, 2019

(30) Foreign Application Priority Data

Apr. 13, 2016 (EP) .................................... 16165130

(51) Int. Cl.
*G01N 21/64* (2006.01)
*G02B 21/00* (2006.01)
(Continued)

(52) U.S. Cl.
CPC ........ *G02B 21/0072* (2013.01); *A61B 5/0059* (2013.01); *G02B 21/002* (2013.01);
(Continued)

(58) Field of Classification Search
CPC .............. G02B 21/002; G02B 21/0056; G02B 21/0072; G02B 21/0076; G02B 26/06;
(Continued)

(56) References Cited

U.S. PATENT DOCUMENTS

2007/0121115 A1* 5/2007 Hill .................... G01B 9/02004 356/450
2009/0084980 A1 4/2009 Mertz
(Continued)

FOREIGN PATENT DOCUMENTS

JP 2011-028208 A 2/2011

OTHER PUBLICATIONS

Booth, M., J., "Adaptive optical microscopy: the ongoing quest for a perfect image," Light: Science & Applications, 3, e165 pp. 1-7 (Apr. 25, 2014).

(Continued)

*Primary Examiner* — Irakli Kiknadze
(74) *Attorney, Agent, or Firm* — Maschoff Brennan

(57) ABSTRACT

It is provided a method for identifying optical aberrations. The method comprising the steps of providing at least one first optical beam and a second optical beam; creating a combined beam by at least partially superimposing the first and the second optical beam; focusing the combined beam into or through a medium and detecting radiation excited in the medium by the combined beam due to nonlinear optical effects; detecting the radiation excited in the medium by the combined beam for each one of the phase positions, the spatial positions and/or the time positions of the first beam; and identifying aberrations using signals generated by a detection device for the plurality of the phase positions, the spatial positions and/or the time positions of the first beam relative to the second beam upon the detection of the radiation excited in the medium.

16 Claims, 2 Drawing Sheets

(51) Int. Cl.
*A61B 5/00* (2006.01)
*G02B 26/06* (2006.01)

(52) U.S. Cl.
CPC ..... *G02B 21/0056* (2013.01); *G02B 21/0076* (2013.01); *G02B 26/06* (2013.01)

(58) Field of Classification Search
CPC .. G02B 21/0032; G02B 21/008; G02B 27/58; C12N 15/1138; C12N 2310/14; G06T 11/60; G06T 2207/10061; G06T 2207/30016; G06T 2207/30148; G06T 7/001; G06T 7/248; G06T 7/337; G06T 7/62; G06T 7/74; G06T 3/4061; G06T 2207/10004; G06T 2207/10056; G06T 7/90; G01N 21/6458; G01N 2201/06113; G01N 2333/71; G01N 33/5308; G01N 33/57492; G01N 1/42; G01N 2021/6417; G01N 21/64; G01N 21/6402; G01N 21/6408; G01N 21/6486; G01N 21/65; G01N 2201/12; G01N 2021/653; G01N 21/6445; G01N 2021/458; G01N 2021/6419; G01N 21/4795; G01N 2201/0675; G01N 21/636; G01N 21/6428; G06K 9/52; G01Q 30/02; G01Q 30/025; G21K 7/00; G01J 2003/1213; G01J 2003/2826; G01J 3/0208; G01J 3/021; G01J 3/0224; G01J 3/0229; G01J 3/0237; G01J 3/08; G01J 3/14; G01J 3/18; G01J 3/2823; G01J 3/32; G01J 3/4406; A61B 5/0059; A61B 3/1015; A61B 3/0025; A61B 3/103; A61B 3/12; A61B 3/112; A61B 3/14; A61B 5/117; A61B 3/0075; A61B 3/028; A61B 18/20; A61B 3/04; A61B 3/1005; A61B 3/107; A61B 3/102; A61B 3/0041; A61B 3/1025; A61B 3/117; A61B 3/1225; A61B 3/152; A61B 5/0068
USPC .......................................................... 250/459.1
See application file for complete search history.

(56) References Cited

U.S. PATENT DOCUMENTS

| | | | | |
|---|---|---|---|---|
| 2009/0137990 | A1 | 5/2009 | Sheinis | |
| 2011/0109962 | A1* | 5/2011 | Cui .................... | G01N 21/6456 359/385 |
| 2013/0015367 | A1 | 1/2013 | Cui | |
| 2015/0077844 | A1 | 3/2015 | Singer et al. | |
| 2016/0003740 | A1 | 1/2016 | Tao et al. | |

OTHER PUBLICATIONS

Booth, M., J., et al., "Adaptive aberration correction in a confocal microscope, " Proceedings of the National Academy of Sciences of the United States of America, vol. 99, Issue 9, pp. 5788-5792 (Apr. 30, 2002).
Judkewitz, B., et al., "Translation correlations in anisotropically scattering media, " Nature Physics, Issue 11, pp. 684-689 (Jun. 29, 2015).
Tang, J., et al., "Superpenetration optical microscopy by iterative multiphoton adaptive compensation technique," Proceedings of the National Academy of Sciences of the United States of America, vol. 109, Issue 22, pp. 8434-8439 (May 29, 2012).
Vellekoop, I., M., and A., P., Mosk, "Focusing coherent light through opaque strongly scattering media," Optics Letters, vol. 32, Issue 16, pp. 2309-2311 (Aug. 15, 2007).
Wang, C., et al., "Multiplexed aberration measurement for deep tissue imaging in vivo," Nature Methods, Issue 11, pp. 1-7 (Aug. 17, 2014).
Wang, K., et al., "Rapid adaptive optical recovery of optimal resolution over large volumes," Nature Methods, vol. 11, Issue 6, pp. 625-628 (Apr. 13, 2014).
Yaqoob, Z., et al., Optical phase conjugation for turbidity suppression in biological samples, Nature Photonics, pp. 110-115 (2008).
European Search Report dated Nov. 3, 2016 as received in Application No. 16165130.2.
Freund, I., et al., "Memory Effects in Propagation of Optical Waves through Disordered Media", American Physical Society, Physical Review Letters, vol. 61, Issue 20, pp. 2328-2331 (Nov. 14, 1988).
Ji, N., et al., "Adaptive optics via pupil segmentation for high-resolution imaging in biological tissues," Nature Methods, vol. 7, No. 2, pp. 141-147 (Dec. 27, 2009).

* cited by examiner

METHOD AND ARRANGEMENT FOR IDENTIFYING OPTICAL ABERRATIONS

CROSS-REFERENCE TO A RELATED APPLICATION

This application is a National Phase Patent Application of International Patent Application Number PCT/EP2017/058806, filed on Apr. 12, 2017, which claims priority of European Patent Application Number 16165130.2, filed on Apr. 13, 2016.

BACKGROUND

The invention relates to a method for identifying optical aberrations and to an arrangement for identifying optical aberrations.

Optical aberrations restrict the properties (e.g. the resolution) of optical systems such as, e.g. confocal microscopes. For example, aberrations induced by a sample limit the imaging depth; e.g. these aberrations are the reason why confocal microscopes or two-photon microscopes cannot be used for investigating regions of a biological tissue sample beyond a certain depth.

A variety of methods for aberration correction in inhomogeneous media such as a biological tissues is known. For example, the article Ji, N., Milkie, D. E. & Betzig, E. "Adaptive optics via pupil segmentation for high-resolution imaging in biological tissues", Nature Methods 7, 141-147 (2009) discloses a pupil segmentation technique, wherein the back aperture of a microscope objective is optically conjugated onto a wavefront shaping element. The back aperture of the objective is then separated into a set of segments and the correction at each segment is calculated by finding a phase pattern on the wavefront-shaping element that maximizes a two photon signal at the imaging plane. However, this method is rather slow and the number of corrected wavefront segments is low (<50) such that its applicability for practical (e.g. biomedical) imaging is limited.

SUMMARY

The object of the invention is to facilitate the implementation of aberration corrections in imaging systems.

This problem is solved by the method comprising features as described herein and the arrangement comprising features as described herein.

According to the invention, a method for identifying optical aberrations is provided, the method comprising the steps of:

a) providing at least one first optical beam and a second optical beam, wherein the intensity of one of the optical beams is higher than the intensity of the other optical beam;

b) creating a combined beam by at least partially superimposing the first and the second optical beam;

c) focusing the combined beam into or through a medium (e.g. a scattering medium) and detecting radiation (e.g. multi-photon excited fluorescence radiation) excited in the medium by the combined beam due to nonlinear effects; wherein d) the first beam is shifted in phase relative to the second beam to a plurality of phase positions, the first beam is spatially displaced relative to the second beam to a plurality of spatial positions and/or the first beam is temporally shifted relative to the second beam to a plurality of time positions;

e) detecting the radiation excited in the medium by the combined beam for each one of the phase positions, the spatial and/or the time positions of the first beam, wherein the radiation is detected by means of a detection device; and f) identifying aberrations using signals generated by the detection device for the plurality of the phase positions, the spatial positions and/or the time positions of the first beam relative to the second beam upon the detection of the radiation excited in the medium.

The first beam may be a spatially scanning beam whose spatial and/or temporal position relative to the second beam is altered, while the second optical beam may be a spatially stationary beam whose spatial and/or temporal position remains unchanged. For example, the intensity of the scanning beam is much higher than the intensity of the stationary beam; e.g. the intensity of the scanning beam is at least three times, at least five times, at least ten times, at least fifty times or at least hundred times the intensity of the stationary beam. It is further noted that the first beam may be spatially displaced and additionally may also be shifted in phase and/or temporally. However, it is also possible that the first beam is only shifted in phase or is only spatially displaced or is only temporally shifted.

For example, the aberrations are identified using first signals generated by the detection device upon detecting radiation for a first phase position, a first spatial and/or a first time position of the first beam and using second signals generated by the detection device upon detecting radiation for a second phase position, a second spatial and/or a second time position of the first beam. Of course, further signals generated for further phase, spatial and/or time positions could be used for identifying the aberrations.

The medium might be a sample that is to be investigated by an optical system (e.g. an imaging system), wherein in step f) optical aberrations related to the medium and/or the optical system are identified. However, it is also possible that the sample to be investigated is different from the medium, wherein the sample might be investigated through the medium. For example, the sample is at least partially arranged on a side of the medium opposite the optical system for investigating the sample. If the sample is different from the medium, in steps e) and f) radiation from the sample might be used in addition to radiation of the medium for identifying aberrations.

Because of the different intensities of the stationary and the scanning beam, the radiation measured for each one of the phase shifts, the spatial and/or time positions of the scanning beam might be assumed to be excited essentially by the scanning beam, only, the intensity of the scanning beam in the imaging plane, however, being modulated due to the interference with the stationary beam. For example, the first and the second beam may have the same wavelength. However, of course, the first and the second beam may have different wavelengths. For example, a phase stepping method could be used (see below) by using slightly different wavelengths of the first and the second optical beam.

For example, the scanning beam exhibits at least one peak of its field amplitude, which might be further amplified due to nonlinear interactions (e.g. multi-photon such as two-photon absorption) of the scanning beam with the medium. The scanning beam thus may be regarded as acting like a delta function, which, due to the interference with the stationary beam, probes the field of the stationary beam. The measured intensity of the radiation excited in the medium (e.g. a signal generated by a photodetector used for detecting the radiation) can be shown to be proportional to the field of the (aberrated) stationary beam such that information about aberrations can be derived from the photodetector signal. It is noted that radiation generated by in principle any kind of nonlinear effect (such as SHG, THG, CARS, FWM and multi-photon absorption) might be detected for carrying out the method according to the invention.

More particularly, the intensity I(x) of a two-photon excited fluorescence radiation caused by the combined beam at medium location x is given by $$I(\chi)=\sigma\cdot\int|E_{scan}(\chi-\chi')+E_{stat}(\Omega')|^4 d\chi' \quad (1)$$

wherein $E_{scan}$ is the field of the first (scanning) optical beam and $E_{stat}$ is the field of the second (stationary) optical beam, the scanning beam being spatially displaced and a is a scaling factor that contains contributions such as the absorption cross-section of the fluorescent medium, detector efficiency etc and can be omitted from following equations without loss of generality. For simplicity, the medium fluorescence is assumed to be quasi-uniform near the stationary focus. This assumption is not required when the stationary beam is the stronger beam.

If the beam powers are set such that $$|E_{scan}| \gg |E_{stat}|\left(\text{e.g. } \frac{|E_{scan}|}{|E_{stat}|} > 10\right),$$

equation (1) reads:

$$I(x) = \int|E_{scan}(x-x')|^4 dx' + 2\int|E_{scan}(x-x')|^2 E^*_{scan}(x-x')E_{stat}(x')dx' + 2\int|E_{scan}(x-x')|^2 E_{scan}(x-x')E^*_{stat}(x')dx' \quad (2)$$

As mentioned above, the scanning optical beam can be assumed to be a "peaky" function, i.e. its field amplitude $|E_{scan}|$ comprises at least one distinct maximum. Thus, the third power term in the second integral of formula (2) above resembles a delta function such that I(x) can be approximated by $$I(\chi)=I_b(\chi)+aE_{stat}(\chi)+aE^*_{stat}(\chi) \quad (3)$$

$I_b$ being the first integral in expression (2).

Formula (3) reveals that the aberrated field of the stationary beam can be inferred from the fluorescence radiation intensity measured by the photodetector; i.e. aberrations that are experienced by an optical field when trying to focus into or through a (e.g. inhomogeneous) medium can be derived on the basis of the photodetector signals.

It is noted that the above explications relate to a spatial displacement of the scanning beam relative to the stationary beam. However, similar considerations are valid when a scanning beam is used that is shifted temporally relative to the (temporally) stationary beam. Thus, the scanning beam, whose intensity is higher than the intensity of the stationary beam, is scanned temporally against the stationary beam and because of the nonlinear interaction of the combined beam, the temporal profile of the time-aberrated stationary beam and thus time-aberrations caused by the medium and/or the imaging system can be derived. It is also conceivable that both spatial and temporal aberrations are identified (e.g. by displacing the first beam spatially and shifting the first beam temporally).

It is further noted that it is also possible that the intensity of the stationary beam is higher than the intensity of the scanning beam, wherein the above reasoning applies analogously. It is also conceivable that both the first and the second optical beam are scanning beams, i.e. beams that are displaced spatially and/or shifted temporally.

According to an embodiment of the invention, identifying aberrations according to step f) comprises determining a point spread function (PSF) of the medium and/or an optical system used for investigating the medium or through the medium (and/or of a sample if the medium is not the sample to be investigated). In particular, the PSF is derived from the photodetector signal, which according to above equation (3) can be assumed to be proportional to the field $E_2$ of the aberrated stationary beam and thus contains the PSF.

Moreover, e.g. for determining the PSF, at least a first and second measurement of the radiation is carried for each one of the spatial positions of the second beam, wherein the relative phase between the first and the second beam is altered between the first and the second measurement. In other words, a phase stepping method is used for extracting information about the aberration from the photodetector signal. For example, a first set of measurements (scanning a pre-determined field of view) is carried out, wherein after completion of the first set of measurements, the phase between the first and the second beam is changed and a second set of measurements is carried out. Of course, more than two sets of measurements may be used.

More particularly, the phase stepping method is used to isolate the contribution of the relevant second term in the above equation (2) similarly to plane wave interferometry where the phase between the object and the reference beam, in this case between the scanning and the stationary beam, is changed in a number of steps, e.g. minimum of 3, more usually of 4, around the unit circle. Setting the phase difference (phase shift) between the two beams at $\Delta\phi_i=0$, $\pi/2$, $\pi$, $3\pi/2$ we get $$I_i(x) = \int|E_{scan}(x-x')|^4 dx' + 2\int|E_{scan}(x-x')|^2 E^*_{scan}(x-x')E_{stat}(x')e^{-i\Delta\phi_i}dx' + 2\int|E_{scan}(x-x')|^2 E_{scan}(x-x')E^*_{stat}(x')e^{i\Delta\phi_i}dx' \quad (4)$$

Combining the four measurements in a way such that $I_f(x)=(I_1-I_3)+i(I_2-I_4)$ we get $$I_f(\chi)=8\cdot\int|E_{scan}(\chi-\chi')|^2 E^*_{scan}(\chi-\chi')E_{stat}(\chi')d\chi' \quad (5)$$

The identified aberrations, e.g. the identified PSF, may be used for adapting the wavefront of the first optical beam; i.e. the wavefront of the scanning beam is adapted (corrected), wherein measurements might be carried out using the corrected beam. The wavefront adaptation may be carried out using a wavefront shaping device, wherein the wavefront shaping device imprints a phase pattern associated to the determined PSF onto the wavefront of the first and/or the second optical beam. The phase pattern may be calculated by means of a Fourier transform of the aberration field determined (e.g. estimated) by means of the signals of the detection device.

The aberrations (e.g. the shape of the PSF) may be numerically estimated using the signals of the detection device (e.g. similar to blind deconvolution), for example using the signals generated for a first set of spatial locations of the scanning beam, wherein these signals may be evaluated for generating an image as already set forth above and the estimate is made on the basis of the image.

Regarding the determination of the PSF the following is noted:

Assuming that a plane wave is incident on a back focal plane of a lens (or any other optical system) for focusing light through an inhomogeneous medium, a diffraction limited spot at a front focal plane of the lens would be generated under perfect conditions. However, due to the presence of the inhomogeneous medium between the lens and the focusing plane, instead of a diffraction limited spot, the result at the focusing plane is an aberrated focus with a complex field. Focusing through an inhomogeneous medium is equivalent to multiplying the input wavefront by the Fourier transform of an aberrated field at a back aperture of the focusing system and then inverse Fourier transforming the result (to obtain the field in the focusing plane of the focusing system).

Using the Fourier transform of equation (5) above it is obtained:

$$\mathcal{F}\{I_f\}=8\,\mathcal{F}\{|E_{scan}(\chi)|^2E^*_{scan}(\chi)\}\cdot\mathcal{F}\{E_{stat}(\chi)\} \tag{6}$$

Using the complex conjugate as the input to the focusing system, at the focusing plane we will have $$E_{at\ focus\ plane}\sim\mathcal{F}^{-1}\{\mathcal{F}\{|E_{scan}(\chi)|^2E^*_{scan}(\chi)\}^*\cdot\mathcal{F}\{E_{stat}(\chi)\}^*\cdot\mathcal{F}\{E_{stat}(\chi)\}\}. \tag{7}$$

Using $$\mathcal{F}\{E_{stat}(\chi)\}^*\cdot\mathcal{F}\{E_{stat}(\chi)\}=1.$$

yields $$E_{at\ focus}(\chi)\sim|E_{scan}(\chi)|^2E^*_{scan}(\chi). \tag{8}$$

Further, the aberrations may be determined iteratively, wherein identifying aberrations according to step f) comprises determining an estimate of the aberrations (e.g. a first estimate of the PSF) on the basis of the signals of the detection device; correcting the first beam by correcting the wavefront of the first beam (which might be the beam with the higher intensity) using the estimate (in particular using a wavefront shaping device as mentioned above); and repeating steps d) to f) using the corrected first beam in order to get an improved estimate of the aberrations (e.g. an improved second estimate of the PSF). Of course, steps d) to f) can be repeated more than once using the previous estimate of the aberrations (and thus the most current correction of the wavefront) for each repetition. After each correction of the scanning beam, the shape of the scanning beam will be closer to a delta function. Accordingly, the determined aberration will converge towards the actual aberration field in the imaging plane. After some repetition (for example, less than ten), the first beam corrected using the final identified aberration may have a diffraction-limited focus in the imaging plane.

Using above equation (8), during a first iteration, the field of the scanning beam is equal to the aberrated PSF, i.e. $E_{scan}(x)=E_{aber}(x)$. Therefore after the first iteration, the field of the corrected scanning beam will be similar to $$E_{corr}(\chi)\sim|E_{aber}(\chi)|^2E^*_{aber}(\chi)=|E_{aber}(\chi)|^3e^{-i\phi aber(\chi)}$$

with the power contained in $E_{corr}$ being equal as in $E_{aber}$

In the case of a thick inhomogeneous media the determined aberration (e.g. the corresponding phase pattern) may be only valid for a certain region around a center position of the scanning beam. The lateral range of the validity is defined by the so-called memory effect range as described, for example, in the article Freund, I., Rosenbluh, M. & Feng, S., "Memory effects in propagation of optical waves through disordered media", Phys. Rev. Lett. 61, 2328-2331 (1988).

Therefore, multiple stationary (second) beams located on different positions within the field of view of the scanning beam could be used in order to multiplex the identification of the aberrations at different locations. Such a pattern of stationary focused spots across the field of view of the scanning beam can be generated using, for example, a lenslet array, a diffractive optical element and/or a spatial light modulator. The appropriate phase patterns that are needed for focusing a corrected beam at different areas within the field of view can be multiplexed on a wavefront shaping device; for example, by superimposing a plurality of phase pattern (each one assigned to a particular region within the field of view) on the wavefront shaping device (e.g. by means of complex summation). It is also possible that the phase patterns are projected sequentially, wherein the phase pattern assigned to a region of the filed of view is projected when the scanning beam is in that region of the field of view.

It is again noted that the above embodiments might be analogously used for determining time aberrations. For example, multiple temporally stationary beams might be used.

The first and the second optical beam may be pulsed beams. For example, the first and the second beam is produced by splitting a pulsed beam originating from a laser light source (e.g. a pulsed laser such as a femtosecond laser).

The invention is also related to an arrangement for identifying optical aberrations, in particular for carrying out the method as described above, the arrangement comprising

- a beam generating device for generating at least one first optical beam and a second optical beam in such a way that the intensity of one of the optical beams is higher than the intensity of the other optical beam;
- a superimposing arrangement for at least partially superimposing the first and the second optical beam;
- a focusing device for focusing the combined beam into or through a medium and a detecting device for detecting radiation excited in the medium by the combined beam due to nonlinear effects;
- a scanning device for phase shifting the first beam relative to the second beam (B2) to a plurality of phase positions, for spatially displacing the first beam relative to the second beam to a plurality of spatial positions and/or for temporally shifting the first beam relative to the second beam to a plurality of time positions, wherein the detecting device is configured in such a way that the radiation excited in the medium by the combined beam is detected for each one of the phase positions, the spatial and/or time positions of the first beam; and
- an evaluation device configured for identifying aberrations using signals generated by the detecting device for the plurality of the phase positions, the spatial positions and/or the time positions of the first beam upon detection of the radiation excited in the medium.

Of course, embodiments of the method according to the invention described above, can be analogously realized in the arrangement according to the invention. For example, the beam generating device comprises a light source for generating an optical beam and a beam splitter for splitting the optical beam into the first and the second optical beam. For example, the light source is a (e.g. pulsed) laser as already mentioned above. The evaluation device for example is realized by a programmed device (such as a computer or a microprocessor).

Further, the arrangement according to the invention may comprise a wavefront shaping device configured for shaping the wavefront of the first and/or second optical beam and/or a temporal profile shaping device for shaping the temporal profile of the first and/or second optical beam using the aberrations identified by the evaluation device. The wavefront shaping device, for example, comprises a deformable mirror or a spatial light modulator. The temporal profile shaping device might be a pulse shaper (e.g. comprising a combination of a diffractive optical element and a wavefront shaping component).

The invention further relates to an optical system (e.g. an imaging system) comprising the arrangement described above. For example, the optical system is scanning microscope device. However, the invention can be used with any kind of an optical device. In particular, the arrangement according to the invention can be used in any optical system that allows the insertion of a wavefront shaping device. It is noted that the first and/the second optical beam may be provided by the optical system, i.e. the first and/the second optical beam may be both used for investigating the medium (or a sample through the medium) and for identifying aberrations.

Moreover, the arrangement according to invention may comprise a device for varying the optical path of the first and/or the second optical beam such as a delay line.

BRIEF DESCRIPTION OF THE DRAWINGS

Embodiments of the invention are described hereinafter with reference to the drawings.

DETAILED DESCRIPTION

Figure 1:
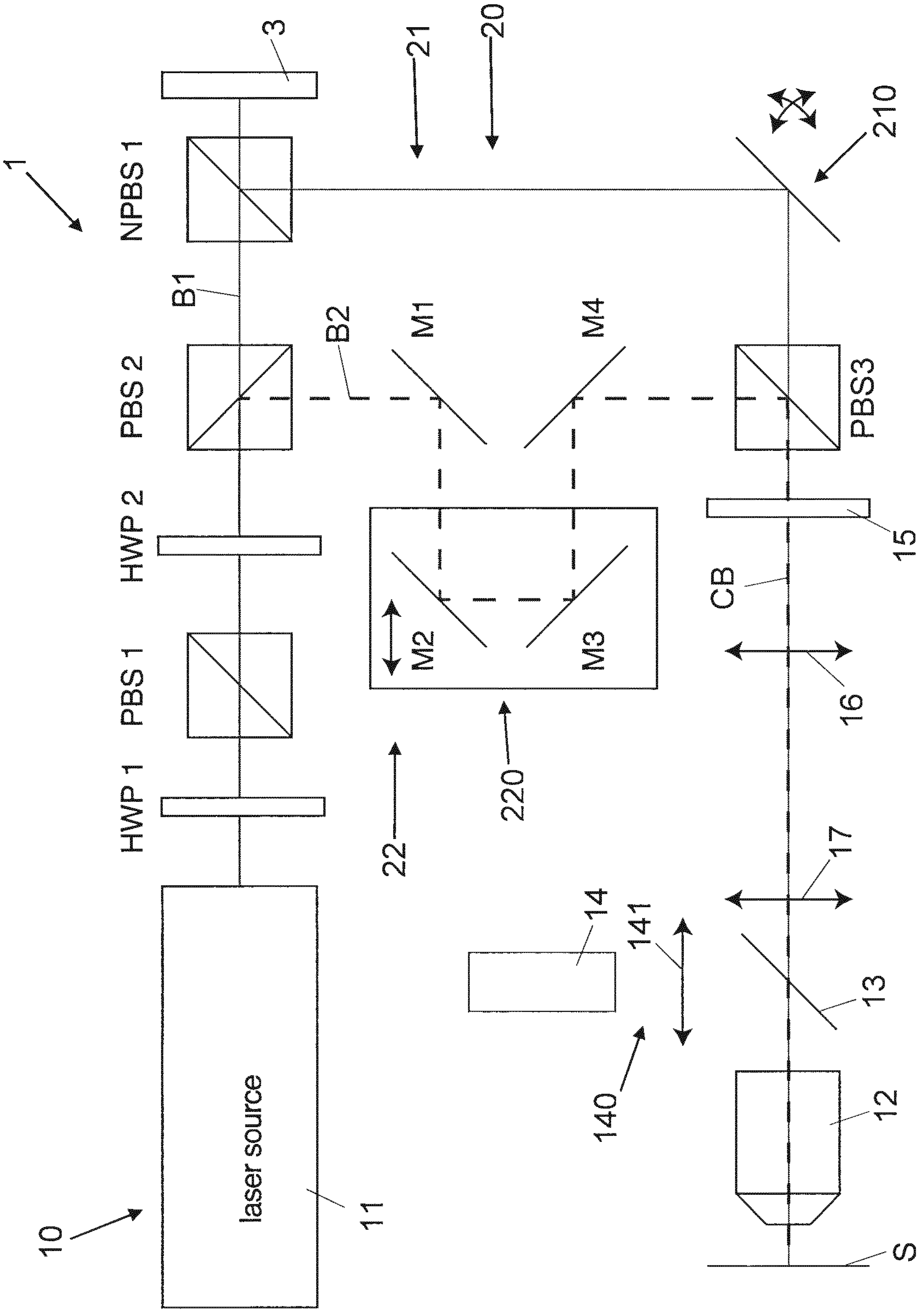
FIG. 1 shows schematically an imaging system comprising an arrangement for identifying aberrations according to an embodiment of the invention.

FIG. 1 illustrates an optical imaging system 10 that may be e.g. operated as a scanning microscope system for investigating biological samples. The optical imaging system 10 comprises an arrangement 1 according to an embodiment of the invention, the arrangement 1 being configured for identifying aberrations of the imaging system 10 and/or the sample to be investigated.

Arrangement 1 comprises an interferometer arrangement 20 having an input beam splitter (polarizing beam splitter PBS 2) that splits an incoming beam generated by a pulsed laser 11 (e.g. a femtosecond laser) into a first and a second optical beam B1, B2. The laser 11 and the beam splitter PBS 2 thus form a beam generating device. The beam generated by laser 11 may be transmitted through further optical components such as half wave plates HWP 1, HWP 2 and a polarizing beam splitter PBS 1. The interferometer arrangement 20 has a first and a second branch 21, 22 providing an optical path for the first and a second beam B1, B2, respectively. The first interferometer branch 21 comprises a beam splitter NPBS 1 (e.g. a non-polarizing beam splitter) and a galvo scanner 210 for deviating the first optical beam. The second interferometer branch 22 has a delay line 220 realized by four deflecting mirrors M1-M4 for adapting the optical path length of the second interferometer branch 22 and thereby changing the phase of the second optical beam B2 relative to the phase of the first optical beam B1. Other phase shifting elements like piezo-scanners, acousto-optic modulators and/or electro-optic modulators might be used instead of or in addition to the delay line 220.

The second optical beam B2 is superimposed with the first optical beam B1 by means of a superimposing arrangement in the form of an output beam splitter PBS 3 of the interferometer arrangement 20, beam splitter PBS 3 being arranged behind the delay line 220 and the galvo scanner 210. The superimposition of the first and the second B1, B2 generates a combined beam CB that is focused into a medium in the form of a sample S using a focusing device in the form of an objective 12, wherein the combined beam CB (i.e. its components consisting of the interfering first and second beam B1, B2) will be aberrated by the sample S. The combined beam CB excites fluorescence radiation in the sample S that is radiated through the objective 12 and reflected by a dichroic mirror 13 into a photodetector 14 of a detection device 140. A detector lens 141 may be arranged in front of the detector 13. Further, the combined beam CB is reflected onto a back aperture of the objective 12 through a polarizer 15, a scan lens 16 and a tube lens 17.

Using the galvo scanner 210, which e.g. comprises two tiltable galvo mirrors, the first beam B1 is spatially displaced, while the second beam B2 remains stationary, i.e. the first beam B1 is a scanning beam and the second beam B2 is a stationary beam. More particularly, the first beam B1 is displaced relative to the second beam B2 to a plurality of locations relative to the second beam B2 and on the sample S. That is, the first beam portion of the combined beam CB is raster scanned onto the image plane while the second beam portion of the combined beam CB is kept stationary on a fluorescent location of the sample. It is noted that the invention is of course not restricted to a certain type of scanning device. For example, the galvo scanner may comprise separate galvo mirrors or non-separated galvo mirrors. It is also possible that piezo mirrors or MEMS mirrors are used.

Further, the arrangement 1 is configured in such a way that the first (scanning) beam B1 has a much higher intensity than the second beam B2 such that the detected fluorescence radiation can be considered as being essentially excited by the intensity of the first beam B1, only. This effect is amplified because the imaging system 10 (e.g. the detection device 140) is configured for detecting radiation excited due to nonlinear effects (e.g. by multi-photon such as two-photon absorption). Therefore, the first beam B1 may be regarded as having a delta function like intensity profile relative to the second beam B2 and thus as probing the profile of the second beam B2 (in the imaging plane of objective 12) as already set forth above.

The fluorescence radiation created by the combined beam CB and detected by the detector 14 thus comprises information about the aberration induced by the sample S. This information can be extracted from the signals generated by the detector 14 upon receipt of fluorescence radiation, e.g. by a phase stepping method. That is, a first set of fluorescence radiation measurements is carried out, wherein the first beam is displaced to a plurality of positions (defining a field of view), while the position of the second beam remains fixed. For example, the position of the second beam is chosen in such a way that it remains focused on a fluorescent spot of the sample S within the field of view of the first beam B1. After completing the first set of measurements, a second set of measurements may be carried out, wherein the second beam B2 is phase shifted relative to the first beam by displacing mirrors M2 and M3 of the delay line 220 before starting the second measurements. The spatial location of the second beam, however, may remain unchanged. The first and the second set of measurements is then used for determining information about the aberration induced by the sample S. For example, the point spread function is derived from the measurements as already describe above. Of course, more than two sets of measurements could be carried out. An evaluation unit (not shown), e.g. a programmed device, may be used for evaluating the detector signals and for deriving the aberration.

The arrangement 1 moreover comprises a wavefront shaping element 3 for shaping the wavefront of the first beam B1. More particularly, a phase pattern derived from the identified aberration is applied to the first beam B1 via the wavefront shaping element 3 such that an aberration corrected beam is generated. In principle, any type of a wavefront shaping element could be employed; for example, a (e.g. liquid crystal) spatial light modulator, a deformable mirror device or a digital micro mirror display. Further, similarly to the first beam B1 also the second beam B2 might be corrected using the identified aberrations. For example, a second wavefront shaping element (not shown) is provided for correcting the second beam B2.

The first beam B1 may be transmitted through beam splitter NPBS 1 to the wavefront shaping element 3, wherein the corrected beam is reflected by the beam splitter NPBS 1 towards the galvo scanner 210. It is noted that if no wavefront shaping element 3 is used a mirror could be used instead of beam splitter NPBS 1 for reflecting the first beam onto the galvo scanner 210.

The aberration corrected first beam B1 may be used for carrying out measurements with the imaging system 10 or for further improving the accuracy of the determined aberration. For example, a first aberration (e.g. a first point spread function) is estimated on the basis of a first measurement and the first aberration is used for correcting the first beam B1 by means of the wavefront shaping element 3. Subsequently, a second measurement is carried out a second aberration is estimated on the bases of the second measurement. That is, the aberration is determined iteratively, wherein, of course, more than two iteration could be used. Using the aberration correction provided by arrangement 1, it might be possible to generate a corrected first beam B1 that creates an only diffraction limited focus spot even in an inhomogeneous sample.

It is noted that multiple second beams B2 might be used as explained above.

Figure 2B:
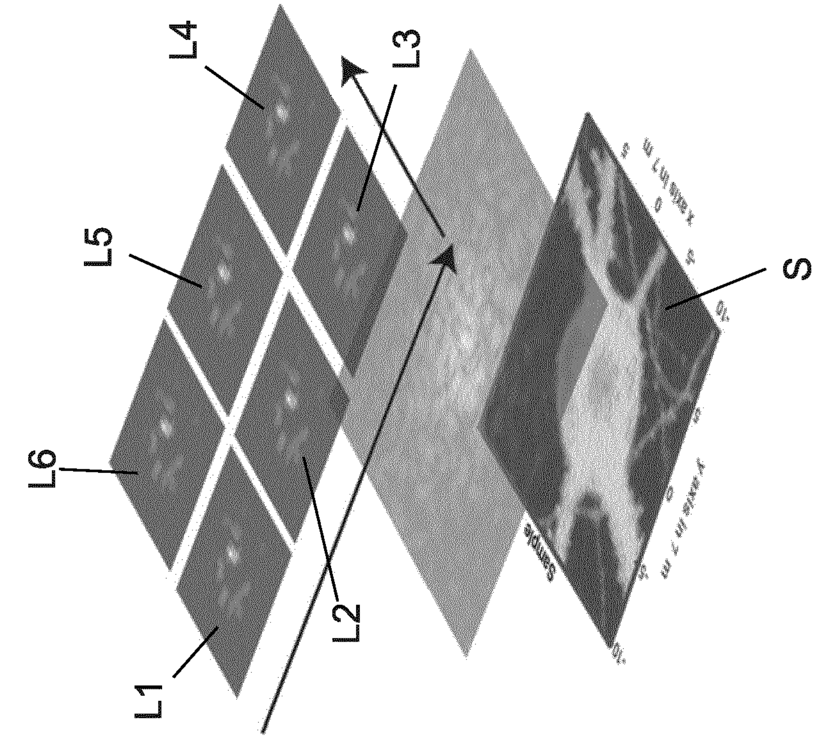
FIG. 2B shows a simulation of two-photon fluorescence radiation excited by a combined beam created by superimposing a scanning beam and a stationary beam.
Figure 2A:
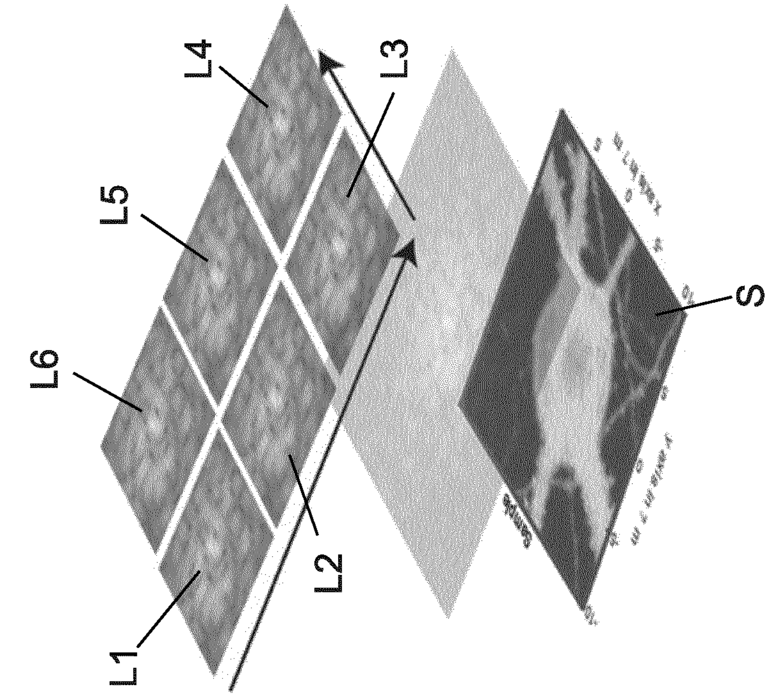
FIG. 2A shows a simulation of conventional fluorescence radiation excited by a combined beam created by superimposing a scanning beam and a stationary beam.

FIG. 2A exemplarily depicts a simulation of fluorescence radiation excited in different locations $L_1$-$L_6$ of a sample S by a scanning beam (first beam B1 in FIG. 1) overlapped with a stationary beam (second beam B2 in FIG. 1) in the case of linear excitation (i.e. in the case of the excitation of conventional fluorescence radiation).

FIG. 2B is related to the case that a non-linear (e.g. two-photon) excitation takes places and that in addition the intensities of the scanning and the stationary beam are different. As set forth above, in that case the scanning beam (of higher intensity) can be described as a delta-like function probing the stationary beam. The fluorescence radiation measured for the different position of the sample S (i.e. for the different positions of the scanning beam) thus carries information of the aberrated complex field that excites the fluorescence radiation, wherein the aberrated complex field can be recovered from the photodetector signal and information about the sample aberration can be derived as described above.

The invention claimed is:

1. A method for identifying optical aberrations, comprising the steps of:

a) providing at least one first optical beam and a second optical beam, wherein the intensity of one of the optical beams is higher than the intensity of the other optical beam;

b) creating a combined beam by at least partially superimposing the first and the second optical beam;

c) focusing the combined beam into or through a medium and detecting radiation excited in the medium by the combined beam due to nonlinear optical effects; wherein d) the first beam is shifted in phase relative to the second beam to a plurality of phase positions, the first beam is spatially displaced relative to the second beam to a plurality of spatial positions and/or the first beam is temporally shifted relative to the second beam to a plurality of time positions;

e) detecting the radiation excited in the medium by the combined beam for each one of the phase positions, the spatial positions and/or the time positions of the first beam, wherein the radiation is detected by means of a detection device; and f) identifying aberrations, using a processor, the aberrations being identified using signals generated by the detection device for the plurality of the phase positions, the spatial positions and/or the time positions of the first beam relative to the second beam upon the detection of the radiation excited in the medium.

2. The method as claimed in claim 1, wherein the aberrations are identified using at least first signals generated by the detection device upon detecting radiation for a first phase position, a first spatial and/or a first time position of the first beam and using second signals generated by the detection device upon detecting radiation for a second phase position, a second spatial and/or a second time position of the first beam.

3. The method as claimed in claim 1, wherein identifying aberrations according to step f) comprises determining a point spread function.

4. The method as claimed in claim 1, wherein at least a first and second measurement of the radiation excited in the medium is carried for each one of the spatial positions of the first beam, wherein the relative phase between the first and the second beam is altered between the first and the second measurement.

5. The method as claimed in claim 1, wherein the identified aberrations are used for correcting the wavefront of the first and/or second optical beam in order to obtain a corrected first and/or second beam.

6. The method as claimed in 5, wherein the corrected first and/or second beam is used as a measurement beam for investigating the medium.

7. The method as claimed in claim 1, wherein identifying aberrations according to step f) comprises determining an estimate of the aberrations on the basis of the signals of the detection device; correcting the first beam by correcting the wavefront of the first beam using the estimate; and repeating steps d) to f) using the corrected first beam in order to get an improved estimate of the aberrations.

8. The method as claimed in claim 1, wherein multiple second beams are provided for generating the combined beam.

9. The method as claimed in claim 1, wherein the intensity of one of the optical beams is at least three times, at least five times or at least ten times the intensity of the other optical beam.

10. The method as claimed in claim 1, wherein the first optical beam is a scanning beam and the second optical beam is stationary.

11. The method as claimed in claim 1, wherein the first and the second optical beam are pulsed beams.

12. An arrangement for identifying optical aberrations comprising:

a beam generating device for generating at least one first optical beam and a second optical beam in such a way that the intensity of one of the optical beams is higher than the intensity of the other optical beam;

a superimposing arrangement for at least partially superimposing the first and the second optical beam to form a combined beam;

a focusing device for focusing the combined beam into or through a medium and a detecting device for detecting radiation excited in the medium by the combined beam due to nonlinear optical effects;

a scanning device for phase shifting the first beam relative to the second beam to a plurality of phase positions, for spatially displacing the first beam relative to the second beam to a plurality of spatial positions and/or for temporally shifting the first beam relative to the second beam to a plurality of time positions, wherein the detecting device is configured in such a way that the radiation excited in the medium by the combined beam is detected for each one of the phase positions, the spatial positions and/or the time positions of the first beam; and an evaluation device comprising a processor configured for identifying aberrations using signals generated by the detecting device for the plurality of the phase positions, the spatial positions and/or the time positions of the first beam relative to the second beam upon detection of the radiation excited in the medium.

13. The arrangement as claimed in claim 12, wherein the beam generating device comprises a light source for generating an optical beam and a beam splitter for splitting the optical beam into the first and the second optical beam.

14. The arrangement as claimed in claim 12, further comprising a wavefront shaping device configured for shaping the wavefront of the first and/or second optical beam and/or a temporal profile shaping device for shaping the temporal profile of the first and/or second optical beam using the aberrations identified by the evaluation device.

15. The arrangement as claimed in claim 12, further comprising a device for varying the optical path of the second optical beam.

16. An optical system comprising the arrangement as claimed in claim 12.

* * * * *